(12) United States Patent
Deline

(10) Patent No.: US 11,079,369 B2
(45) Date of Patent: Aug. 3, 2021

(54) DEVELOPMENT OF DRY-DEPOSIT TRACE EXPLOSIVES DETECTION TEST STANDARDS, SOLUTIONS AND METHODS FOR DEPOSITION

(71) Applicant: The Government of the United States of America, as represented by the Secretary of Homeland Security, Washington, DC (US)

(72) Inventor: James E. Deline, Egg Harbor City, NJ (US)

(73) Assignee: The Government of the United States of America, as represented by the Secretary of Homeland Security, Washington, DC (US)

( * ) Notice: Subject to any disclaimer, the term of this patent is extended or adjusted under 35 U.S.C. 154(b) by 317 days.

(21) Appl. No.: 16/037,692

(22) Filed: Jul. 17, 2018

(65) Prior Publication Data
US 2019/0025274 A1    Jan. 24, 2019

Related U.S. Application Data

(60) Provisional application No. 62/534,273, filed on Jul. 19, 2017.

(51) Int. Cl.
*G01N 1/38* (2006.01)
*G01N 33/22* (2006.01)
*G01N 1/28* (2006.01)

(52) U.S. Cl.
CPC ......... *G01N 33/227* (2013.01); *G01N 1/2813* (2013.01); *G01N 1/38* (2013.01); *G01N 2001/2893* (2013.01)

(58) Field of Classification Search
CPC .................. G01N 1/2813; G01N 1/38; G01N 2001/2893; G01N 33/227
See application file for complete search history.

(56) References Cited

U.S. PATENT DOCUMENTS 5,092,220 A * 3/1992 Rounbehler ....... G01N 33/0037
                                                89/1.1
6,470,730 B1 10/2002 Chamberlain

* cited by examiner

*Primary Examiner* — Alexander M Weddle
(74) *Attorney, Agent, or Firm* — Lavanya Ratnam; Kelly G. Hyndman; Robert W. Busby

(57) ABSTRACT

Various embodiments of the present invention are directed towards a system and method to dispense an explosive compound onto a substrate. An example device includes a solvent having the explosive compound dissolved in the solvent to form a sample. A delivery mechanism dispenses the sample in a dispersed manner to sufficiently vaporize the solvent to prevent wicking while dispersing a residue of the explosive compound on the substrate to enable detection by explosive detection tools.

2 Claims, 5 Drawing Sheets

```
                    ┌─────────┐
                    │  Start  │──── 501
                    └────┬────┘
                         ▼
    ┌────────────────────────────────────────────┐
    │ Dissolve explosive compound in solvent to  │──── 502
    │ form sample                                │
    └────────────────────┬───────────────────────┘
                         ▼
    ┌────────────────────────────────────────────┐
    │ Pressurize sample in canister              │──── 504
    └────────────────────┬───────────────────────┘
                         ▼
    ┌────────────────────────────────────────────┐
    │ Dispense, using delivery mechanism, sample │
    │ in dispersed manner to enable vaporization │──── 506
    │ of solvent and formation of residue of     │
    │ explosive compound                         │
    └────────────────────┬───────────────────────┘
                         ▼
    ┌- - - - - - - - - - - - - - - - - - - - - -┐
    │ Actuate delivery mechanism to form residue │──── 508
    │ of explosive compound in predefined pattern│
    └- - - - - - - - - - -┬- - - - - - - - - - -┘
                         ▼
                    ┌─────────┐
                    │   End   │──── 510
                    └─────────┘
```

FIG. 5

DEVELOPMENT OF DRY-DEPOSIT TRACE EXPLOSIVES DETECTION TEST STANDARDS, SOLUTIONS AND METHODS FOR DEPOSITION

CROSS-REFERENCE TO RELATED APPLICATIONS

This application claims the benefit of U.S. Provisional Application No. 62/534,273 entitled "Development of Dry-Deposit Trace Explosives Detection Test Standards, Solutions and Methods for Deposition," filed on Jul. 19, 2017, the contents of which are incorporated herein by reference in their entirety.

STATEMENT OF GOVERNMENT INTEREST

The present invention was made by one or more employees of the United States Department of Homeland Security in the performance of official duties, and, thus the claimed invention may be manufactured, used, licensed by or for the United States without the payment of any royalties thereon.

FIELD OF THE INVENTION

The present invention relates generally to the field of explosives detection, and more particularly to the field of producing test samples for explosives detection.

BACKGROUND OF THE INVENTION

Test samples for trace explosives detection can be produced based on a "dry transfer" technique, such as the technique disclosed in U.S. Pat. No. 6,470,730 directed to a dry transfer method for the preparation of explosives test samples, involving pipetting an explosives solution onto a non-reactive strip and allowing the solution's solvent to dry. The strip is then rubbed onto another surface to transfer the explosive to the other surface. The explosive thus transferred to the other surface is harvested using explosives trace detection system sampling media, which is analyzed by an explosives detection system. The intermediate step of dry-transferring the explosive to the non-reactive strip, rather than depositing the explosives solution directly onto the other surface, is to avoid unwanted interactions of the solvent with the other surface.

Such steps of solvent deposition of explosives solution onto the non-reactive strip, drying of the strip and solvent, and mechanical transfer of the explosive from the non-reactive strip to the other surface/substrate are labor intensive and introduce the potential for errors. The efficiency of such steps can be different for different types/combinations of explosives and substrates. Avoiding a need for such steps can result in significant labor savings, and can result in standards that are a closer approximation to naturally occurring explosives contamination.

SUMMARY OF THE INVENTION

In an example embodiment, a device is configured to dispense an explosive compound onto a substrate, e.g., as an explosive residue that can be detected by an explosives testing system. The device includes a solvent and the explosive compound dissolved in the solvent to form a sample. A delivery mechanism of the device is to dispense the sample in a dispersed manner to enable vaporization of the solvent and formation of a residue of the explosive compound on the substrate. The dispersed manner prevents the solvent from interacting with the substrate to undermine trace explosive detection test and evaluation of the substrate.

In another example embodiment, a verification system is configured to test explosives detection systems. The verification system includes a plurality of devices. A given device is configured to dispense its respective corresponding explosive compound onto a substrate. The given device includes a solvent and the explosive compound dissolved in the solvent to form a sample. A delivery mechanism is to dispense the sample in a dispersed manner to enable vaporization of the solvent and formation of a residue of the explosive compound on the substrate. The dispersed manner prevents the solvent from interacting with the substrate in a manner that would undermine trace explosive detection test and evaluation of the substrate. The dispenser is configured to accept insertion of at least one of the plurality of devices to facilitate dispensing of its corresponding sample. The plurality of devices included in the verification system serve as a corresponding plurality of explosive compounds representing at least those types of explosive compounds capable of being detected by the explosives detection system.

In yet another example embodiment, a method to dispense an explosive compound onto a substrate includes dissolving the explosive compound in a solvent to form a sample, pressurizing the sample in a canister, and dispensing, using a delivery mechanism, the sample in a dispersed manner to enable vaporization of the solvent and formation of a residue of the explosive compound on the substrate. The dispersed manner prevents the solvent from interacting with the substrate in a manner that would undermine trace explosive detection test and evaluation of the substrate.

Other features and aspects of the invention will become apparent from the following detailed description, which taken in conjunction with the accompanying drawings illustrate, by way of example, the features in accordance with embodiments of the invention. This summary is not intended to identify key or essential features of the claimed subject matter, nor is it intended to limit the scope of the invention, which is defined solely by the claims attached hereto.

BRIEF DESCRIPTION OF THE DRAWINGS

One or more example embodiments of the present invention are described in detail with reference to the following drawings. These drawings are provided to facilitate understanding of the present invention and should not be read as limiting the breadth, scope, or applicability thereof. For purposes of clarity and ease of illustration, these drawings are not necessarily made to scale.

FIG. 5 illustrates a method of dispensing an explosive compound according to an example.

Figure 1:
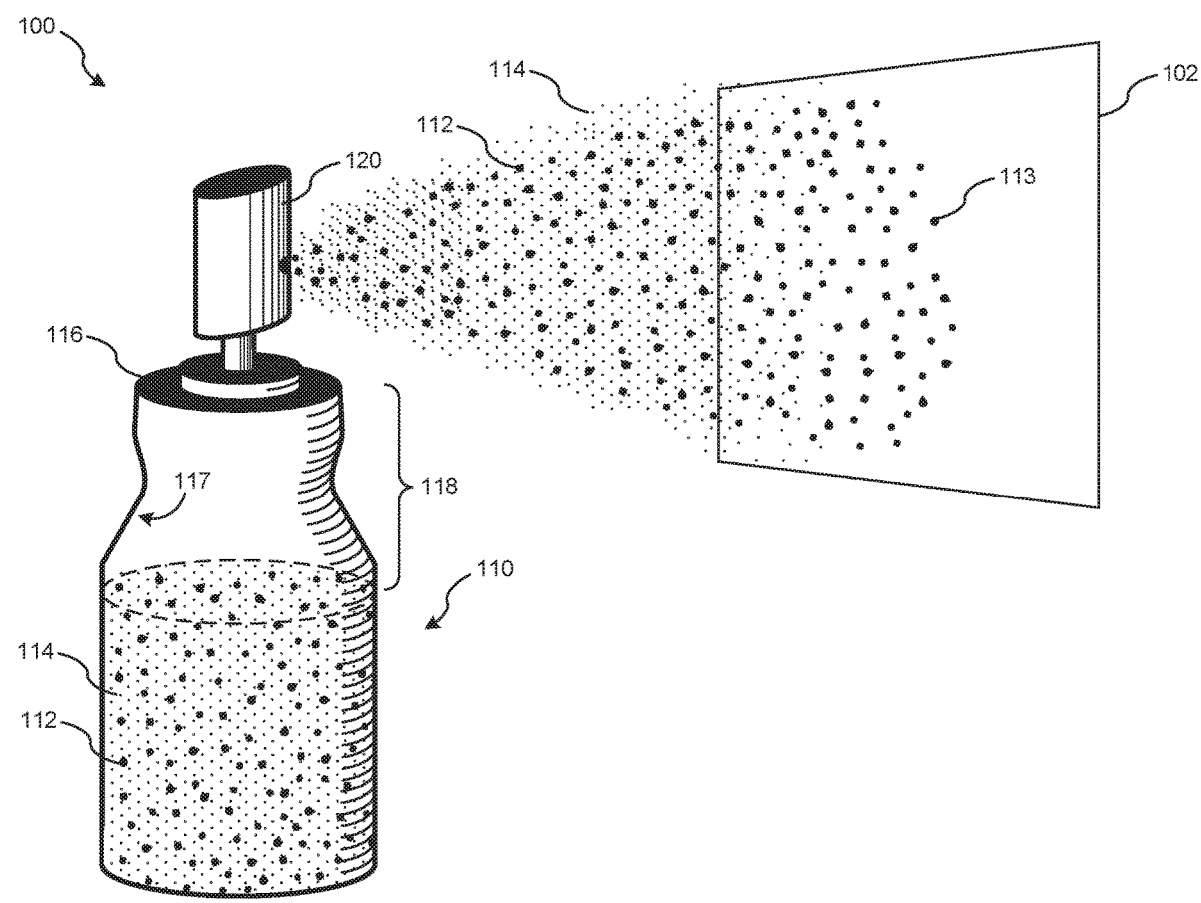
FIG. 1 illustrates a device to dispense an explosive compound according to an example.

These drawings are not intended to be exhaustive or to limit the invention to the precise form(s) disclosed. It should be understood that the present invention can be practiced with modification and alteration, and that the invention is limited only by the claims and the equivalents thereof.

DETAILED DESCRIPTION OF THE INVENTION

Examples described herein involve devices and methods to dispense explosive compounds. An explosive compound can be dissolved in a solvent(s), which can act as a pressurized liquid to be used for dispensing the dissolved explosive compound. An example solvent can exist as a gas at room temperature, such that it evaporates rapidly and therefore does not allow enough time to interact with a substrate on which the explosive compound is being dispensed. Furthermore, the rapid evaporation means test samples can be prepared without needing a waiting time for liquid evaporation to complete, enabling "just in time" (JIT) preparation of samples for testing. Containers of the dissolved explosives can be prepared and conveniently sent out in a ready-for-use condition. Test article preparation can be automated, e.g., using robotics to prepare an article to be tested, based at least in part on the capability of accurately dispensing small volumes of a sample under moderate pressure.

Explosives can be dissolved in a solvent, such as hydrofluoroalkane (HFA), and dispensed under pressure directly onto various test substrates. The solvent rapidly evaporates and the explosive residue is free of solvent. The residue can be harvested and tested with a commercial off-the-shelf (COTS) trace explosives detection system (ETD). Such approaches obviate a need to perform the various steps that can be involved in dry-transfer techniques to prepare the test samples for such ETDs, including deposition of a solution of dissolved explosives onto a non-reactive test strip such as Teflon®, evaporation of the solvent from the Teflon® strip, and dry-transfer of the dried explosive from the test strip onto a test substrate for the ETD to test. Explosives dissolved in solvents prepared for such dry-transfer techniques use the non-reactive test strip, and are not deposited as dissolved solvents directly onto test substrates, because of incompatibility with the test substrates and wicking issues or other such interactions between the liquid solvent and the test substrates that would interfere with or undermine trace explosive detection test approaches (e.g., by also causing a visual indication of where the solvent touched the test substrate). Unlike such approaches, the examples described herein can use a propellant/solvent that dissipates virtually instantaneously upon being dispensed, or can be sprayed/delivered in a manner that sufficiently spreads or otherwise does not enable the solvent to interact with the substrate in a manner that would interfere with the ETD testing, such as by avoiding wicking or other alteration of the substrate. Thus, it is possible to use solutions of explosive(s) in solvent(s) to, for example, produce "dry" explosives standards for trace explosives detection test and evaluation (T&E) of vendor systems.

FIG. 1 illustrates a device 100 to dispense an explosive compound 112 according to an example. The device 100 is configured to dispense the explosive compound 112 onto a substrate 102. The explosive compound 112 is dissolved in the solvent 114 to form a sample 110. The device 100 includes a delivery mechanism 120, to dispense the sample 110 in a dispersed manner. As illustrated, the dispersed manner enables vaporization of the solvent 114, including vaporization before, upon, and/or after contacting the substrate 102, because vaporization can occur before the solvent 114 has an opportunity to contact the substrate 102. A residue 113 of the explosive compound 112 is formed on the substrate 102. The dispersed manner in which the sample 110 is applied prevents the solvent 114 from interacting with the substrate 102 to undermine trace explosive detection test and evaluation of the substrate 102. For example, the liquid form of the solvent 114 does not have an opportunity to accumulate at levels sufficient to cause wicking in the substrate 102, which might create a visual indication where the solvent 114 came in contact and changed the surface morphology of the substrate 102 to interfere with collection of the residue 113 of the explosive compound 112. In another example, the sample 110 is dispensed in a dispersed manner to enable the solvent 114 to rapidly evaporate in the air and/or evaporate from the substrate 102 without wicking, while leaving behind the explosive compound 112 in the form of finely dispersed dry particles, which form the residue 113 of the explosive compound 112 on the substrate 102.

The delivery mechanism 120 enables the device 100 to dispense the sample 110 in a dispersed manner, e.g., to enable dry-application of trace amounts of the explosive compound 112 onto the substrate 102 as the residue 113. The ability to achieve the dispersed manner is based not only on the features of the delivery mechanism 120, but also on the properties of the sample 110 including the properties of the explosive compound(s) 112 and solvent(s) 114, as well as the pressure in the canister 116 (which can be affected by, e.g., vapor pressure of the solvent(s) 114). For example, the ability of the explosive compound 112 to travel further to reach the substrate 102, when dispensed, than the solvent 114 which evaporates before reaching that travel distance. In an example, the residue 113 of the explosive compound 112 includes particles having an average particle size of approximately six microns. Various examples can vary and/or combine different characteristics to achieve the dispersed delivery of the explosive compound 112, including varying: a predetermined solubility of the explosive compound 112 in one or more solvents 114 (such as HFA), a dispersal/spreading of mechanical spraying technique, a ratio of solvent to solute, a volume of accurately dispensed sample solution to be sprayed, boiling point of the solvent, a pressure of the sample 110 and velocity of delivery, relative size/weight difference between the particles of the explosive compound 112 vs. the solvent(s) 114, and other factors to affect the resulting ability to harvest and detect the delivered explosive compounds 112 directly deposited onto test substrates 102, without allowing the solvent(s) 114 to cause appreciable interference with the substrate 102. Such factors can be varied to prevent the solvent(s) 114 from interacting with the substrate 102. For example, a spray dispersal can be widened to diffuse a given solvent 114 sufficiently to prevent the solvent 114 from negatively interacting with the substrate 102, while still allowing the explosive compound 112 to reach the substrate 102 in sufficient concentrations.

In an example, the solvent 114 is hydrofluoroalkane (HFA), which can include different versions of HFA. For example, HFA 134a solvent has a boiling point of −26 degrees Celsius and is a liquid under pressure (e.g., a pressure of approximately 70-80 psi) at room temperature, but is a gas under atmospheric pressure at room temperature. HFA 134a therefore has characteristics that enable it to serve as a solvent, and also to serve as a propellant, to enable dispersal of the explosive compound 112. HFA 134a also has a characteristic of flash-evaporating very quickly, enabling the sample 110 to leave behind small, dry particles of the explosive compound 112 that were previously in solution with the HFA 134a. Thus, samples 110 based on the solvent HFA 134a, or other solvents having characteristics that can be used by the device 100 to provide similar effects, can be used to effectively dry-apply trace amounts of explosive compounds 112 directly onto test surfaces (e.g., residue 113 on substrate 102).

In another example, the solvent 114 is HFA 227. HFA 227 is an alternative to HFA 134a. Multiple grades of HFA 134a and 227 exist, such as refrigerant, extraction, and pharmaceutical grades. The grade of solvent used is based on the resulting stability of the solutions of various types of explosive compounds. For example, the stability of explosives dissolved in refrigerant-grade HFA 134 a was found to be sufficient for most types of explosive compounds. The stability of the solution can be influenced by using different types and/or grades of solvents, e.g., based on given levels of impurities corresponding to given grades of the solvents, which may affect rates of decomposition of the explosive compounds in the solutions, depending on the types of explosive compounds used to form the solutions. Non-HFA solvents, which cannot be used in a pharmaceutical application, can be used with this invention. One such solvent is dimethyl ether (DME), which is a liquid under pressure but a gas at room temperature and pressure.

Example samples 110 can involve multiple different types and/or grades of solvents 114 used together. For example, a solvent 114 can serve multiple functions, serving as a propellant, in addition to being used to affect solubility. In an example, the solvent 114 can include a first solvent 114, to dissolve the explosive compound 112 corresponding to a first solubility and to serve as a propellant for the delivery mechanism 120, and can include a second solvent 114 that, in combination with the first solvent 114, dissolves the explosive compound 112 corresponding to a second solubility greater than the first solubility (see FIG. 4 for example levels of solubility in example solvents). In an example, a second solvent 114, which can be referred to as a co-solvent, can be ethanol, which also has the benefit of low human toxicity. Because the solutions of samples 110 as described herein are not intended to be consumed or inhaled, a wide variety of co-solvents can be used (e.g., those solvents that are not specifically associated with low human toxicity). Some of the various solvents that can be used, either alone or in combination with other solvents as a co-solvent, include acetone, methanol, tetrahydrofuran, acetonitrile, ethanol, and the like. Examples described herein can use solvents and/or co-solvents that, when not used with an example delivery mechanism 120, would otherwise be expected to cause an issue for interactions with the substrate. For example, due to the approach of dispensing as described herein in a dispersed manner while allowing the explosive compound 112 to substantially be deposited on the substrate 102, even those solvents that would otherwise interact with the substrate 102 are prevented from interacting with the substrate 102 by virtue of the dispersed dispensing of the delivery mechanism 120. An example solution might involve two percent of such a co-solvent being used in a solution of 50 microliters (μL) total, such that dispensing results in only 1 μL of the co-solvent thereby being spread over a relatively large dispersed area of the substrate 102, and therefore is prevented from interfering with the substrate 102 in a manner that would undermine trace explosive detection test and evaluation of the substrate 102. For example, by avoiding wicking of the solvent 114 on the substrate 102, the substrate 102 is not visually marked where the residually deposited explosive compound 112 is located. Accordingly, an agent conducting a test cannot visually tell where the explosive compound residue 113 may have been deposited, and the substrate 102 is not mechanically altered by the solvent 114 in a way that would prevent the explosive compound residue 113 from being collected by a test swabbing procedure. In an example, a first solvent 114 might only provide a first solubility of less than a threshold solubility to enable the resulting residue to be sufficient for trace explosive detection test and evaluation. Accordingly, a second solvent 114 can be used to provide a second solubility of at least the threshold solubility sufficient for trace explosive detection test and evaluation. The second solubility thereby enables the explosive compound 112, when dispensed, to form a residue 113 sufficient for the trace explosive detection test and evaluation to be performed on the substrate 102.

In the illustrated example of FIG. 1, the delivery mechanism 120 comprises a canister 116 that includes an interior coating 117. The canister 116 is comprised of aluminum and the interior coating 117 is formed by passivation of the aluminum interior surface of the canister 116. In the example of FIG. 1, the pressurization of the canister 116 can be due, at least in part, to the internal vaporization pressure generated by the solvent(s) 114). In other examples, the delivery mechanism 120 can include other types of pressurized delivery of the sample 110, such as based on a pressurized pump delivery. Example canisters 116 can be formed of different materials, including other types of metals, or other materials such as plastic or resin. The illustrated delivery mechanism 120 includes an inert headspace 118, which enables a propellant (such as vaporization of HFA solvent serving as the propellant) to develop sufficient pressure for effective dispersal consistent with achieving a desired deposit of residue 113 and vaporization of the solvent 114. The headspace 118 can be formed by evacuation of residual oxygen prior to sealing the canister 116, thereby improving stability of the solutions. Removal of oxygen, and/or coating the inside 117 of the canister 116, helps prevent solution decomposition that might occur via interactions, such as interactions with oxygen and/or metal.

In one example, the delivery mechanism 120 comprises a specially configured and pressurized metered dose inhaler (pMDI) which has been configured to dispense a measured volume of the sample that, in view of a concentration of the explosive compound in the sample and other factors such as sample solubility and pressure, dispenses the sample 110 to form a threshold detectable amount of the residue 113 of the explosive compound 112 on the substrate 102. An MDI crimping station can be used to crimp a valve onto the MDI prior to being pressurized. A pressure filler can be used to fill and/or pressurize the MDI containers with the sample 110.

The various examples described herein provide many benefits, including elimination of a need for earlier approaches used to deposit explosive compounds 112 on substrates 102, such as those approaches that needed an intermediate dry-transfer step and the use of Teflon® transfer strips, which were associated with additional quality-assurance verification steps to verify that threshold quantities of explosive compounds were actually deposited and/or transferred from solution to test strip and from test strip to substrate. Additionally, production of the test strips required hours of labor and an inert atmosphere to dry the strips in a special-built drying chamber. Once dried, the strips needed to be used quickly, because the explosive compounds deposited on the strips could decompose. Unlike such earlier approaches, the examples described herein enable test samples to be prepared "just-in-time," because there is no need to wait for solvent to dry. The sample 110 can be sprayed onto a surface/substrate 102 and then immediately subject to a test procedure, e.g., harvested with sampling/ swabbing media. Accordingly, the examples described herein obviate a need to produce large trays of test strips that need to be used immediately or discarded, thereby conserving resources and labor.

Figure 2:
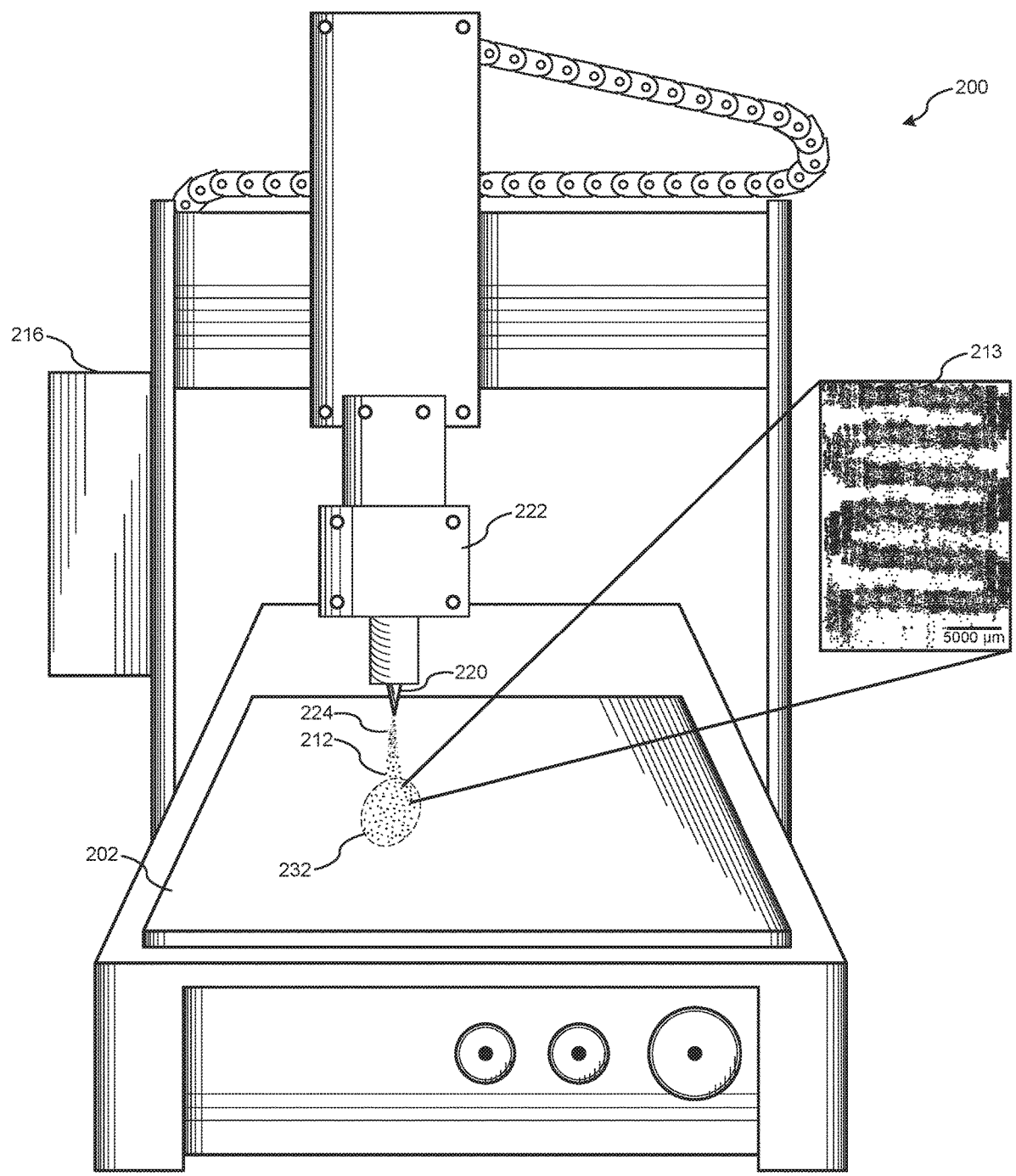
FIG. 2 illustrates a computer-controlled robotic actuator device to dispense an explosive compound according to an example.

FIG. 2 illustrates a computer-controlled robotic actuator device 200 to dispense an explosive compound 212 according to an example. A solution of solvent(s) and explosive compound(s) 212 can be stored in a container 216 capable of handling a pressure sufficient to generate, in conjunction with the delivery mechanism 220 (e.g., valve), the desired dispersal appropriate for explosives testing procedures (e.g., on the order of 100 pounds per square inch (psi)). The container 216 is plumbed to a delivery mechanism 220, e.g., a dispensing valve such as a PICO® sprayer valve produced by Nordson EFD, which is capable of dispensing the sample under pressure (up to 1500 psi) with accuracy and precision, and controlled by a computer to open and close the delivery mechanism 220 for an amount of time calculated to dispense the desired amount of solution and achieve a desired dispersed delivery of the explosive compound 212 onto the substrate 202 as explosive residue 213. The example device 200 also comprises a computer-controlled robotic actuator 222, to actuate the delivery mechanism 220 to dispense nanodroplets 224 (e.g., nanoliter droplets) of the sample, to be deposited as explosives compound residue 213 onto the substrate surfaces 202 in, e.g., a predefined pattern. The substrate 202 (alternative to actuator 222 and/or in conjunction with actuator 222) also can be actuated, e.g., by a robotic "XYZ table" to achieve a predefined dispensing pattern based on movement of the table, whether the actuator 222 is stationary and/or actuated. For example, a computer-controlled valve 220 can be supported stationary above an actuated XYZ table, and the XYZ table (along with the substrate 202) can be actuated to create the predefined pattern 232. The predefined pattern provides a benefit of duplicating how "in-the-field" explosives contamination would occur in a given environment. For example, the computer-controlled dispensing valve 220 can be configured to open and close for an amount of time that, in view of a pressure and a concentration of the explosive compound 212 in the sample, forms a threshold detectable amount the residue 213 of the explosive compound 212 on the substrate 202 consistent with what would be deposited by a human fingerprint of someone who handled the explosive. In an example usage of the device 200, residue 213 of an explosives compound can be printed directly onto glass and Teflon®, and/or into gas chromatography (GC) vials. A relatively low percent of relative standard deviation (RSD) is achievable (<5%) through the use of the actuator device 200. For example, a solution of the explosive compound RDX is achievable from the use of the solvents HFA-134a/acetonitrile (ACN). Dispensing such a sample solution on a 1"×1" glass section enabled an average residue 213 particle size of 6 microns.

Figure 3:
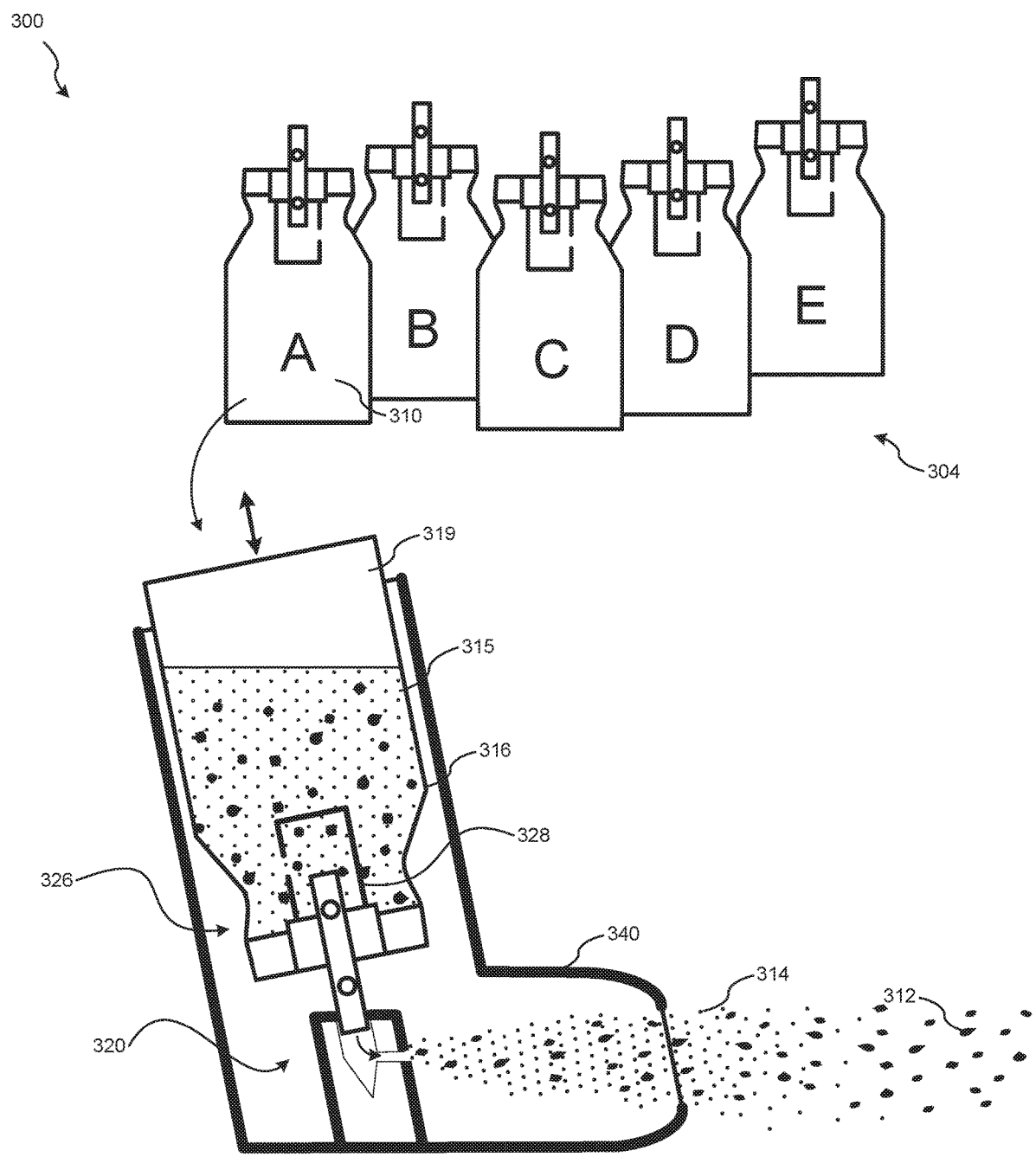
FIG. 3 illustrates a verification system to test explosives detection systems based on dispensing a plurality of explosive compounds according to an example.

FIG. 3 illustrates a verification system 300 that is configured for use in testing explosives detection systems (not shown), based on dispensing a plurality of explosive compounds (e.g., the illustrated example samples A, B, C, D, and E contained in a plurality of devices 304) according to an example. The example verification system 300 includes a plurality of devices 304 containing various sample solutions A-E of explosive compounds. A given device 304 contains a sample 310 (five samples A-E are shown, although example systems 300 can include a greater or fewer number of devices/samples depending on which explosive compounds are to be used for testing a given explosives detection system). A device 304 is configured to dispense its respective corresponding explosive compound 312 onto a substrate or directly onto the vendor-supplied harvesting media. The given device includes a solvent(s) 314, which can be one or more solvents as described above. The explosive compound(s) 312 is dissolved in the solvent(s) 314 to form the sample 310. The canister 316 is configured to safely contain the sample 310 as a gas phase 319 and as a liquid phase 315 at a range of temperatures and pressures including those of atmospheric pressure at room temperature.

A given one of the plurality of devices 304 includes a delivery mechanism 320 to dispense the sample in a dispersed manner, enabling vaporization of the solvent 314 and formation of a residue of the explosive compound 312 on a substrate (not shown in FIG. 3). The delivery mechanism 320 can include aspects located in the device 304 and also located in the dispenser 340 in which the device 304 is inserted. The delivery mechanism 320 includes a valve 326 and retaining cup 328, and can include an expansion chamber to facilitate dispersal of the sample. The canister 316 is depicted as being installed into the dispenser 340, such that an output of the canister 316 feeds into an expansion chamber of the dispenser 340.

The dispenser 340 is configured to accept insertion of at least one of the plurality of devices 304 to facilitate dispensing of its corresponding sample 310. The plurality of devices 304 includes a plurality of explosive compounds, respectively, representing at least those types of explosive compounds capable of being detected by the explosives detection system that is to be tested using the verification system 300. Accordingly, different systems 300 can be configured and distributed to different sites according to the type of explosives detection systems located at the sites.

The plurality of devices 304 are filled with samples having solutions of explosives at predefined concentrations to deliver a sufficient amount of explosive compound 312 on a substrate when the samples are dispensed. In an example, the plurality of devices 304 can include respective valves 326, configured to dispense predefined amounts of sample 310. In an example, the valves are configured to dispense predefined volumes, such as 20, 25, or 50 microliters of solution sample 310 per activation of their respective devices 304/dispenser 340. Depressing the canister 316 toward the dispenser 340 enables the valve 326 to actuate and dispense the corresponding measured quantity of the sample 310. The measured quantity of the sample 310 in turn contains a measured quantity of the explosive compound 312 in accordance with the dissolved concentration in the sample 310. The measured quantity dispensed per valve actuation can also be influenced by the characteristics of the retaining cup 328. Accordingly, different volumes of dispensed solutions can be tailored according to respective concentrations of the sample solutions, e.g., according to different combinations of explosive compound(s) and solvent(s) and resulting solubilities.

In an example usage scenario, the verification system 300 can be used by Transportation Security Administration (TSA) Security Officers (TSOs) at an airport. The system 300 enables various different canisters of the plurality of devices 304, filled with respective samples 310 of various different explosive compounds, to be inserted into the dispenser 340. The inserted canister 316 can be sprayed onto a surface/substrate, which can then be sampled in a fashion known for explosives detection systems (e.g., swabbing with a sampling media). The sampling media can then be inserted into the explosives detection system for analysis. If the system is operating correctly for detecting the given sample 310 of explosive compound, the system should alarm on the given explosive compound being detected. This can be repeated for any number of different explosive compounds contained in the verification system 300, to ensure that the explosives detection system is operating properly and detecting all forms of explosives that the system is rated to detect. In view of this approach, the verification system 300 can be customized to include those plurality of devices 304 containing explosive compounds particularly suited for testing a given explosives detection system, including those compounds not detectable by the explosives detection system, e.g., to confirm the absence of false positive results. Alternatively, the verification system 300 can include a wide variety of explosives compounds, which can be used to compare the relative effectiveness levels of multiple different explosives detection systems. For example, the verification system 300 can be used to test explosives detection systems (ETDs) such as the Morpho Itemiser® DX, the Smiths Detection IONSCAN™ 500DT, and the L3 Security & Detection Systems B220™, which ETDs may show different alarm rates for the various types of explosive compounds in the plurality of devices 304 included in the verification system 300.

The verification system 300 also can be used to verify ETDs when used with various different types of test substrates/items/samples to be tested by the ETDs, while providing more flexibility and wider variety of application compared to previous approaches of preparing test samples. In an example, the verification system 300 was used to prepare ten different test substrates, including those that may present particular difficulties for solvent-based direct-deposited samples. For example, the prepared test substrates included cardboard, foam, fabric, tape, and plastic materials. A high percentage of the samples resulted in successful alarms by the ETDs, demonstrating the usefulness of the variety of applications on which the verification system 300 can be used.

The verification system 300 provides other advantages over prior test preparation approaches, such as the capability of producing test standards/samples outside of laboratory environments. For example, prior test preparation approaches prepared Teflon® strips to contain dried explosive residue, which could not be shipped because the test strips were not durable in the prepared state. Accordingly, if a vendor wanted to perform testing at their own facilities, they would need to perform their own prior dry-transfer test preparation approach using solutions of explosives to prepare the test sample strips on-site. There is some art that comes with experience in performing the prior test preparation approaches to prepare test sample strips, so prior test results would vary widely. However, in contrast to prior test preparation approaches, examples described herein enable the verification system 300, including a plurality of canisters containing calibrated solutions of explosives, to be shipped to the vendor. The vendor can then dispense predictable, reproducible, and precisely controlled aliquots of explosive compound samples directly onto substrate test surfaces, to create consistent test standards without needing the intermediate test strips in order to transfer explosive compounds onto substrates. The valve 326 on the example canisters 316 can be engineered to dispense accurate volumes of samples with high precision. In an example system 300, a given canister 316 can produce approximately 200 test samples, and can be discarded when empty due to the relatively low cost of production.

Figure 4:
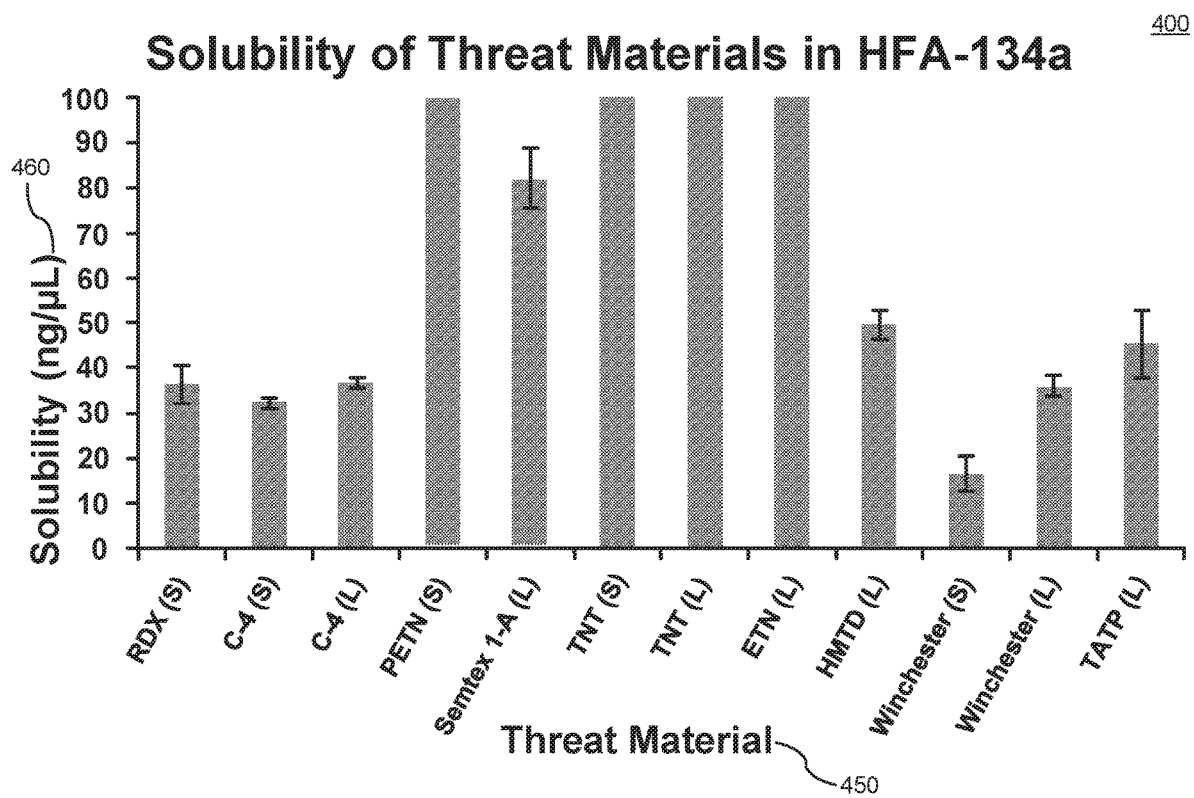
FIG. 4 illustrates a chart of a plurality of explosive compounds and their corresponding respective solubilities according to an example.

FIG. 4 illustrates a chart 400 of a plurality of explosive compounds 450 and their corresponding respective solubilities 460 in HFA solvent according to an example. The illustrated solubilities are shown using various explosive compounds exposed to the solvent of HFA-134a.

The solubility of RDX in HFA 134a (without a co-solvent to modify the solubility) is approximately 35 ng/µL. This concentration is suitable for dispensing the solutions to obtain depositions of explosive compound residues. The solubility can be increased, to dissolve a higher concentration of explosives and obtain higher corresponding residue concentrations, by using even a small amount (e.g., 1-2%) of a co-solvent(s), such as methanol and/or acetonitrile co-solvents. In addition, the stability of the solutions can be increased by using particular approaches in preparing a given canister of a sample explosive compound solution. For example, the interior of the canister can be provided with a coating as described above, and/or an "inert" headspace of the canister can be used, e.g., by evacuation of residual oxygen prior to filling and sealing the canister as described above, to further increase the stability of the sample solutions when used with such prepared canisters.

FIG. 5 illustrates a method 500 of dispensing an explosive compound according to an example. The method starts at block 501. At block 502, at least one explosive compound is dissolved in at least one solvent to form a sample. In an example, an explosive compound such as RDX is dissolved in a mixture of approximately 98-100% of HFA solvent/propellant and 0-2% co-solvent (such as methanol and/or acetonitrile), such that the sample solution exceeds a minimum solubility of the RDX to deliver sufficient quantity of RDX residue when the sample solution is dispensed.

At block 504, the sample is pressurized in a canister. In an example, a crimping station is used to crimp a valve to a canister, and a pressure filler is used to fill the canister with a sample solution at a pressure sufficient to enable the solvent(s) to exist at least partially in a liquid form (e.g., ~70 psi) and enable e valve to deliver a quantity of the sample solution for providing a testable quantity of explosive compound residue when the valve of the canister is dispensed (e.g., ~70-100 psi).

At block 506, the sample is dispensed, using a delivery mechanism, in a dispersed manner to enable vaporization of the solvent and formation of a residue of the explosive compound on the substrate. The dispersed manner prevents the solvent from interacting with the substrate in a way that would undermine trace explosive detection test and evaluation of the substrate. In an example, the sample is dispensed to allow the solvent to rapidly evaporate without time to interact with the substrate, and leave behind finely dispersed dry particles. The sample is dispensed based on a valve configured to deliver a predefined volume of the sample solution, e.g., 20 microliters. The delivery mechanism can involve the use of an actuator/dispenser, which may include an expansion chamber and mouth/throat, to enhance dispersal of the sample when dispensed.

Optionally at block 508, the delivery mechanism is actuated to dispense nanodroplets of the sample to cause formation of the residue of the explosive compound on the substrate in a predefined pattern. The predefined pattern can be a simulated fingerprint, or other pattern, to simulate real-world conditions for realistic explosive detection testing. In an example, the delivery mechanism is a Picovalve® that is robotically controlled to deliver specific measured quantities of the sample solution while moving the delivery mechanism and/or substrate relative to each other to create a simulated fingerprint pattern of residue on the substrate. The method ends at block 510.

While a number of example embodiments of the present invention have been described, it should be appreciated that the present invention provides many applicable inventive concepts that can be embodied in a wide variety of ways. The example embodiments discussed herein are merely illustrative of ways to make and use the invention and are not intended to limit the scope of the invention. Rather, as will be appreciated by one of skill in the art, the teachings and disclosures herein can be combined or rearranged with other portions of this disclosure and the knowledge of one of ordinary skill in the art.

Terms and phrases used in this document, unless otherwise expressly stated, should be construed as open ended as opposed to closed—e.g., the term "including" should be read as meaning "including, without limitation" or the like; the term "example" is used to provide example instances of the item in discussion, not an exhaustive or limiting list thereof; the terms "a" or should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Furthermore, the presence of broadening words and phrases such as "one or more," "at least," "but not limited to," or other similar phrases, should not be read to mean that the narrower case is intended or required in instances where such broadening phrases may be absent. Any headers used are for convenience and should not be taken as limiting or restricting. Additionally, where this document refers to technologies that would be apparent or known to one of ordinary skill in the art, such technologies encompass those apparent or known to the skilled artisan now or at any time in the future.

What is claimed is:

1. A method to dispense an explosive compound onto a substrate, comprising:
    dissolving the explosive compound in a solvent to form a sample;
    disposing the sample in a canister;
    pressurizing the canister;
    coupling the canister to a delivery mechanism, that has a valve, so that the valve couples with the canister;
    actuating the delivery mechanism to open the valve;
    dispensing the sample from the delivery mechanism and toward the substrate in a dispersed manner so as to sufficiently vaporize the solvent, to prevent wicking, while dispersing a residue of the explosive compound on the substrate, to enable detection by explosive detection tools.

2. The method of claim 1, further comprising actuating the delivery mechanism to dispense nanodroplets of the sample to cause formation of the residue of the explosive compound on the substrate in a predefined pattern comprising a simulated human fingerprint.

* * * * *